United States Patent
Takeuchi et al.

(10) Patent No.: US 7,592,298 B2
(45) Date of Patent: Sep. 22, 2009

(54) COMPOSITION FOR OIL-BASED LIQUID CLEANSING

(75) Inventors: Nobuyuki Takeuchi, Yokohama (JP); Yoshihisa Abe, Yokohama (JP)

(73) Assignee: Fancl Corporation, Kanagawa (JP)

( * ) Notice: Subject to any disclaimer, the term of this patent is extended or adjusted under 35 U.S.C. 154(b) by 155 days.

(21) Appl. No.: 11/571,654

(22) PCT Filed: Jul. 1, 2005

(86) PCT No.: PCT/JP2005/012209

§ 371 (c)(1),
(2), (4) Date: Feb. 9, 2007

(87) PCT Pub. No.: WO2006/004041

PCT Pub. Date: Jan. 12, 2006

(65) Prior Publication Data

US 2007/0232515 A1    Oct. 4, 2007

(30) Foreign Application Priority Data

Jul. 6, 2004 (JP) .............................. 2004-198750

(51) Int. Cl.
C11D 3/18 (2006.01)
C11D 3/20 (2006.01)
A61K 8/33 (2006.01)
A61K 8/37 (2006.01)

(52) U.S. Cl. ..................... 510/119; 510/136; 510/432; 510/437; 510/505; 424/401; 424/70.1

(58) Field of Classification Search ................. 510/119, 510/136, 432, 437, 505; 424/401, 70.1
See application file for complete search history.

(56) References Cited

U.S. PATENT DOCUMENTS

2002/0160023 A1* 10/2002 Bagdi et al. ............... 424/401

FOREIGN PATENT DOCUMENTS

| JP | 2003-121259 | 4/2003 |
|---|---|---|
| JP | 2003-267835 | * 9/2003 |
| JP | 2004-075566 | 3/2004 |
| JP | 2005-002047 | 1/2005 |
| JP | 3729836 | 10/2005 |
| JP | 2006-022004 | 1/2006 |

OTHER PUBLICATIONS

Machine translation of JP 2003-267835 from the JPO and translation of paragraphs [0006] and [0014] thereof provided by Applicant, Sep. 2003.

* cited by examiner

*Primary Examiner*—Brian P Mruk
(74) *Attorney, Agent, or Firm*—Knobbe, Martens, Olson & Bear LLP

(57) ABSTRACT

This invention provides an oil-based liquid cleansing preparation that does not sag from the hands during use, can easily be applied to a contemplated site, i.e. has excellent usability, exhibits excellent spreadability during cleansing, gives excellent feeling on use which can realize suitable thickness felling, is usable under an environment where the hands and face are in a wetted state, such as a bathroom and a washstand, has a high level of detergency, and is free from residual oil touch after water washing. This composition comprises an ester of a fatty acid with polyglycerin, glycerin esters of a monocarboxylic acid and a dicarboxylic acid, and a monocarboxylic fatty acid ester which is liquid at 25° C. and has a viscosity of 300 to 3000 mPa·s.

12 Claims, No Drawings

COMPOSITION FOR OIL-BASED LIQUID CLEANSING

This application is the U.S. National Phase under 35 U.S.C. § 371 of International Application PCT/JP2005/012209, filed Jul. 1, 2005, which claims priority to Japanese Patent Application No. 2004-198750, filed Jul. 6, 2004. The International Application was published under PCT Article 21 (2) in a language other than English.

TECHNICAL FIELD

The present invention relates to an oil-based liquid cleansing composition.

PRIOR ART

Oil-based cleansing agents are sold on the market for use in removing dirt and makeups from the skin. These cleansing agents, developed mainly for the purpose of providing cleansing effect, are available in liquid form in many varieties. Conventional oil-based cleansing agents become cloudy when applied to the wet skin as the oil content emulsifies or produces suspended material, and this emulsion or suspended material significantly reduces the cleansing power. However, recent years have seen a number of oil-based liquid cleansing compositions that do not emulsify or increase viscosity considerably even when a significant amount of water mixes into the composition. These products are available on the market for use in an environment where the user's hands and face are likely wet, such as in the bathroom or at the washbasin.

Liquid oil-based cleansing compositions having the aforementioned improved function already contain water, or are designed to accommodate a large amount of water through solubilization. As a result, all these compositions inevitably have low viscosity due to the associated restrictions on permissible formulation. However, these low-viscosity liquid cleansing compositions present problems such as difficulty taking the cleansing agent into the palms, and the cleansing agent dripping down easily through the fingers. These problems make it difficult to apply the cleansing agent to the target area (Patent Literature 1: Japanese Patent Laid-open No. 2004-75566). Also, since low-viscosity oil-based liquid cleansing compositions do not stay firmly attached to the applied area during cleansing, the user ends up rubbing the skin directly with his/her hands and fingers, which can lead to skin irritation or other discomfort during use.

Among the techniques to increase the viscosity of an oil-based liquid cleansing composition, one that uses glyceryl behenate/eicosadioate to prevent the liquid from dripping down through the fingers during use is disclosed (Patent Literature 2: Japanese Patent Laid-open No. 2003-267835). However, no technique is known to date that increases the viscosity of an oil-based liquid cleansing composition in a manner allowing the cleansing agent to be used in an environment where the user's hands and face are set.

Patent Literature 1: Japanese Patent Laid-open No. 2004-75566

Patent Literature 2: Japanese Patent Laid-open No. 2003-267835

Patent Literature 3: Japanese Patent Laid-open No. 2003-121259

SUMMARY OF THE INVENTION

Problems to be Solved by the Invention

The present invention relates to an oil-based cleansing agent characterized by all of the following characteristics: not dripping off the palms during use; easy to use and apply to the target area; spreading well during cleansing; making the user feel smooth by creating a film of appropriate thickness between the user's fingers/hand and skin; fit for use in an environment where the user's hands and face are likely wet, such as in the bathroom or at the washbasin; offering high cleansing power; and leaving no oiliness after the cleansing agent has been rinsed off with water.

Means for Solving the Problem

The key configurations of the present invention are as follows:
1. An oil-based liquid cleansing composition with a viscosity of 300 to 3,000 mPa·s, characterized by containing ester of fatty acid and polyglycerin, glycerin ester of monocarboxylic acid and dicarboxylic acid, and monovalent fatty acid ester that is liquid at 25° C.
2. An oil-based liquid cleansing composition according to 1, characterized in that the monovalent fatty acid ester that is liquid at 25° C. is contained by 40 to 95 percent by weight.
3. An oil-based liquid cleansing composition according to 1 or 2, characterized in that the glycerin ester of monocarboxylic acid and dicarboxylic acid is contained by 0.1 to 7.0 percent by weight.
4. An oil-based liquid cleansing composition according to any one of 1 through 3, characterized in that the ester of fatty acid and polyglycerin is contained by 1.0 to 40.0 percent by weight.
5. An oil-based liquid cleansing composition according to any one of 1 through 4, characterized by containing, as the ester of fatty acid and polyglycerin, polyglycerin medium chain fatty acid ester produced by esterization of medium chain fatty acid with a carbon number of 6 to 10 and polyglycerin with an average degree of polymerization of 3 or above but less than 100.

Effects of the Invention

The present invention provides an oil-based liquid cleansing composition that retains its cleansing function even when wet; does not drip off the palms before applying; spreads well during use, and makes the user feel smooth by creating a film of appropriate thickness between the user's fingers/hand and skin.

The cleansing agent proposed by the present invention can be easily applied to the target area; spreads well during cleansing; makes the user feel smooth by creating a film of appropriate thickness between the user's fingers/hand and skin retains high cleansing power even when used in an environment where the user's hands and face are likely wet, such as in the bathroom or at the washbasin; and can be rinsed off effectively with water.

BEST MODE FOR CARRYING OUT THE INVENTION

Glyceryl behenate/eicosadioate is one form of the glycerin ester of monocarboxylic acid and dicarboxylic acid used in the oil-based liquid cleansing composition proposed by the present invention.

Under the present invention, glycerin ester of monocarboxylic acid and dicarboxylic acid should be contained by 0.1 to 7.0 percent by weight, or preferably by 0.5 to 5.5 percent by weight. If the content is less than 0.1%, viscosity increasing effect cannot be obtained. As a result, the cleansing agent drips down through the fingers during use and cannot be easily applied to the target area. If the content exceeds 7.0%, the cleansing agent does not spread well during cleansing. Also, the skin remains oily after the cleansing agent has been rinsed off, which is undesirable.

The oil-based liquid cleansing composition proposed by the present invention uses ester of fatty acid and polyglycerin. This is a form of nonionic surface active agent. Examples include, among others, polyglycerin isostearate, polyglycerin diisostearate, polyglycerin triisostearate, polyglycerin tetraisostearate, polyglycerin laurate, polyglycerin dilaurate, polyglycerin trilaurate, polyglycerin tetralaurate, polyglycerin caprylate, polyglycerin dicaprylate, polyglycerin tricaprylate, polyglycerin tetracaprylate, polyglycerin palmitate, polyglycerin dipalmitate, polyglycerin tripalmitate, and polyglycerin tetrapalmitate. Its HLB should be in a range of 5 to 15, or preferably 6 to 13, in order to achieve good compatibility with oil agent and dispersibility into water.

Ester of fatty acid and polyglycerin should be contained by 1 to 40 percent by weight, or especially 5 to 25 percent by weight, with respect to the total constituents of the cleansing composition proposed by the present invention. If the content is less than 1%, the composition does not provide sufficient cleansing property and water rinsing property. If the content is greater than 40%, possible negative effects may result such as "fluidity becomes poor and the composition cannot remain in oil-based liquid form" and "the skin feels irritated or receives other discomfort during use."

Among all forms of ester of fatty acid and polyglycerin, particularly favorable is polyglycerin medium chain fatty acid ester produced by esterization of medium chain fatty acid with a carbon number of 6 to 10 and polyglycerin with an average degree of polymerization of 3 or above but less than 100.

A composition containing polyglycerin medium chain fatty acid ester can solubilize a large amount of water and has excellent dispersibility in water. As a result, such composition, if used as an oil-based liquid cleansing cosmetic agent, does not lose its cleansing power even when the skin is wet.

The oil-based liquid cleansing composition proposed by the present invention uses monovalent fatty acid ester that is liquid at 25° C. The monovalent fatty acid ester used in the present invention may be, among others, octyl isononanoate, isononyl isononanoate, isopropyl myristate, isodecil isononanoate, isopropyl palmitate, octyl palmitate, hexyl laureate, octyl isopalmitate, isocetyl octanoate, isopropyl isostearate, ethyl isostearate, cetyl octanoate, stearyl octanoate, and isostearyl octanoate. The monovalent fatty acid ester that is liquid at 25° C. should be contained by 40 to 95 percent by weight. If the content is less than 40%, makeups cannot be lifted effectively from inside the pores in the skin, which makes the composition undesirable as an oil-based liquid cleansing composition. If the content exceeds 95%, it becomes difficult to ensure the intended effects (viscosity and cleansing power).

The viscosity of the oil-based liquid cleansing composition proposed by the present invention is 300 to 3,000 mPa·s at 25° C. when measured by a type B viscometer (rotor No. 2, 12 rpm). If the viscosity is less than 300 mPa·s, the cleansing agent drips down through the fingers during use and cannot be easily applied to the target area. If the viscosity exceeds 3,000 mPa·s, on the other hand, the cleansing agent does not spread effectively. Also, the skin remains oily after the cleansing agent has been rinsed off, which is undesirable.

In addition to the above, silicon oils, paste oils and solid oils can also be used, as long as the effects of the present invention are not negatively affected.

EXAMPLE 1

Next, the present invention is explained in details by using examples. It should be noted, however, that the present invention is not at all limited to these examples.

The cleansing compositions shown in Table 1 were prepared and the property, ease of use, and makeup removing effect when mixed with water, were evaluated for each composition. The results are shown in Table 1.

(Method of Production)

Ester of fatty acid and polyglycerin, and glycerin ester of monocarboxylic acid and dicarboxylic acid, were heated and melted completely, after which both were mixed uniformly to obtain a cleansing composition.

(Method of Evaluation)

(1) Property

Viscosity was measured at 25° C. using a type B viscometer (rotor No. 2, 12 rpm).

(2) Ease of Use (a) "Ease of Application to the Target Area"

An oil-based liquid cleansing composition becomes easier to apply to the target area when the viscosity of the composition is adjusted, thereby making it difficult for the cleansing agent to drip off the palms.

Twenty subjects were asked to evaluate the "ease of application to the target area" during use. The subjects used 2 ml of each cleansing composition.

Evaluation Criteria

◎: At least 15 out of 20 subjects said that the cleansing composition was "easy to apply to the target area."
○: 10 to 14 out of 20 subjects said that the cleansing composition was "easy to apply to the target area."
Δ: 6 to 9 out of 20 subjects said that the cleansing composition was "easy to apply to the target area."
X: Not more than 5 out of 20 subjects said that the cleansing composition was "easy to apply to the target area."

(3)-1 Ease of Use During Cleansing "Ease of Spreading"

Twenty subjects were asked to evaluate the "ease of spreading" of each cleansing agent during use. The subjects used 2 ml of each cleansing composition.

Evaluation Criteria

◎: At least 15 out of 20 subjects said that the cleansing composition "spread well."
○: 10 to 14 out of 20 subjects said that the cleansing composition "spread well."
Δ: 6 to 9 out of 20 subjects said that the cleansing composition "spread well."
X: Not more than 5 out of 20 subjects said that the cleansing composition "spread well."

(3)-2 Ease of Use During Cleansing "Massaging Effect"

An oil-based liquid cleansing composition can make the user feel smooth by creating a film of appropriate thickness between the user's fingers/hand and skin, by means of adjusting the viscosity and selecting appropriate oil agent and surface active agent to be included in the composition. This film of appropriate thickness also provides good massaging effect when the cleansing agent is used, which allows the cleansing agent to pick up makeups effectively. "Massaging effect" refers to ease of use in terms of how effectively the cleansing agent picks up makeups.

Twenty subjects were asked to evaluate the "massaging effect" of each cleansing agent during use. The subjects used 2 ml of each cleansing composition.

Evaluation Criteria

◎: At least 15 out of 20 subjects said that the cleansing composition offered "good massaging effect."
○: 10 to 14 out of 20 subjects said that the cleansing composition offered "good massaging effect."
Δ: 6 to 9 out of 20 subjects said that the cleansing composition offered "good massaging effect."
X: Not more than 5 out of 20 subjects said that the cleansing composition offered "good massaging effect."

(4) Makeup Removing Effect when Mixed with Water

To simulate a condition of use by wet hands, the respective cleansing compositions under Examples and Comparative Examples were mixed with water at a weight ratio of 10 to 3, and the obtained compositions were used as samples to evaluate the makeup removing effect of each cleansing composition based on the evaluation method of cleansing agents specified in Patent Literature 3 (Japanese Patent Laid-open No. 2003-121259). A red lipstick was used as the makeup material. To remove the makeup material, 2 ml of each cleansing composition was used, followed by rinsing off using 400 ml of water.

Skin color was measured before and after the makeup material was applied, and the measured results were indicated by the corresponding values under the L*a*b* color expression method. Next, the makeup material was rinsed off using the cleansing agent, and skin color was measured again using the L*a*b* color expression method. The coordinate distance (R1) between a point in the three-dimensional coordinate system representing the L*a*b* value before application of makeup material, and a point in the three-dimensional coordinate system representing the L*a*b* value after application of makeup material, indicates a condition where the entire amount of makeup material remains. The coordinate distance (R2) between a point in the three-dimensional coordinate system representing the L*a*b* value before application of makeup material, and a point in the three-dimensional coordinate system representing the L*a*b* value after cleansing with the cleansing agent, indicates a condition where some makeup material remains after it has been rinsed off with the cleansing agent. The coordinate distance R between two points in the three-dimensional coordinate system (points I and II) can be calculated using formula 1 shown below:

$$R=[(L*I-L*II)^2+(a*I-a*II)^2+(b*I-b*II)^2]^{1/2} \quad \text{Formula 1}$$

[In the formula, R indicates the coordinate distance between points I and II, while L*I and L*II indicate the brightness levels at points I and II, respectively. Similarly, a*I and b*I, and a*II and b*II indicate the chromaticity levels at points I and II, respectively.]

The residual ratio K of makeup material after cleansing with the cleansing agent can be expressed using formula 2 below:

$$K=R2/R1\times100(\%) \quad \text{Formula 2}$$

The greater the value of K, the more makeup material remains attached, suggesting that the cleansing agent used provides weaker cleansing power.

Evaluation Criteria

◎: The residual ratio of makeup material is less than 10%.
○: The residual ratio of makeup material is 10 or above but less than 15%.
Δ: The residual ratio of makeup material is 15 or above but less than 25%.
X: The residual ratio of makeup material is 25% or above.

(5) Ease of Rinsing with Water "Oiliness After Rinsing with Water"

Twenty subjects were asked to apply each cleansing composition and evaluate the "absence of oiliness after rinsing with water." The subjects used 2 ml of each cleansing composition, followed by 400 ml of water for rinsing.

Evaluation Criteria

◎: At least 15 out of 20 subjects said that the cleansing composition left "no oiliness after rinsing with water."
○: 10 to 14 out of 20 subjects said that the cleansing composition left "no oiliness after rinsing with water."
Δ: 6 to 9 out of 20 subjects said that the cleansing composition left "no oiliness after rinsing with water."
X: Not more than 5 out of 20 subjects said that the cleansing composition left "no oiliness after rinsing with water."

TABLE 1

| | Constituent | Example 1 | Example 2 | Example 3 | Example 4 | Comparative Example 1 | Comparative Example 2 | Comparative Example 3 | Comparative Example 4 | Comparative Example 5 |
|---|---|---|---|---|---|---|---|---|---|---|
| A | Octyl Palmitate | 81 | 80 | 80 | 80 | 82 | 80 | 80 | — | — |
| B | Glyceryl tricapryl/caprate | — | — | — | — | — | — | — | 80 | — |
|   | Olive squalane | — | — | — | — | — | — | — | — | 80 |
| C | Polyglyceryl-6 caprylate | 6 | 6 | — | — | — | — | — | — | — |
|   | Polyglyceryl-10 caprylate | — | — | 6 | — | 6 | — | 6 | 6 | 6 |
|   | Polyglyceryl-20 caprylate | — | — | — | 6 | — | — | — | — | — |
|   | Polyglyceryl-10 diisostearate | — | — | 12 | 12 | 12 | — | 12 | 12 | 12 |
|   | Polyglyceryl-10 laurate | 12 | 12 | — | — | — | — | — | — | — |
| D | PEG-20 glyceryl triisostearate | — | — | — | — | 0 | 18 | — | — | — |
| E | Dextrin palmitate | — | — | — | — | 0 | 2 | 2 | — | — |
| F | Glyceryl behenate/eicosadioate | 1 | 2 | 2 | 2 | — | — | — | 2 | 2 |
|   | Viscosity (mPa·s) | 320 | 650 | 1250 | 2000 | 40 | 1200 | 120 | 2400 | 2600 |
|   | Ease of application to target area | ◎ | ◎ | ◎ | ◎ | X | ◎ | Δ | ◎ | ◎ |
|   | Ease of spreading | ◎ | ◎ | ◎ | ◎ | ○ | ○ | ○ | ○ | X |
|   | Massaging effect | ◎ | ◎ | ◎ | ◎ | Δ | ○ | Δ | Δ | X |
|   | Cleansing power when mixed with water | ◎ | ◎ | ◎ | ◎ | ◎ | X | ○ | X | X |
|   | Oiliness after rinsing with water | ◎ | ◎ | ◎ | ◎ | ○ | Δ | ○ | X | X |

A: Monovalent fatty acid ester that is liquid at 25° C.
B: Oil agent other than monovalent fatty acid ester that is liquid at 25° C.
C: Ester of fatty acid and polyglycerin
D: Surface active agent other than ester of fatty acid and polyglycerin
E: Viscosity increasing agent
F: Glycerin ester of monocarboxylic acid and dicarboxylic From the above results, the oil-based liquid cleansing compositions provided by Examples do not drip off the palms during use; are easy to use and apply to the target area; spread well during cleansing; make the user feel smooth by creating a film of appropriate thickness between the user's fingers/hand and skin; are fit for use in an environment where the user's hands and face are likely wet, such as in the bathroom or at the washbasin; offer high cleansing power; and leave no oiliness after the cleansing agent has been rinsed off with water.

The invention claimed is:

1. An oil-based liquid cleansing composition with a viscosity of 300 to 3,000 mPa-s, comprising as three major components an ester of fatty acid and polyglycerin contained by 1.0 to 40.0 percent by weight, a glycerin ester of monocarboxylic acid and dicarboxylic acid contained by 0.1 to 7.0 percent by weight, and a monovalent fatty acid ester that is liquid at 25° C. contained by 40 to 95 percent by weight.

2. The oil-based liquid cleansing composition according to claim 1, characterized by containing, as the ester of fatty acid and polyglycerin, polyglycerin medium chain fatty acid ester produced by esterization of medium chain fatty acid with a carbon number of 6 to 10 and polyglycerin with an average degree of polymerization of 3 or above but less than 100.

3. An oil-based liquid cleansing composition having a viscosity of 300 to 3,000 mPa-s, consisting essentially of:
   an ester of fatty acid with polyglycerin contained by 1.0 to 40.0 percent by weight;
   a glycerin ester of monocarboxylic acid with dicarboxylic acid contained by 0.1 to 7.0 percent by weight; and
   a monovalent fatty acid ester that is liquid at 25° C. contained by 40 to 95 percent by weight.

4. The oil-based liquid cleansing composition according to claim 3, wherein the glycerin ester monocarboxylic acid with dicarboxylic acid is contained by 0.5 to 5.5 percent by weight.

5. The oil-based liquid cleansing composition according to claim 3, wherein the ester of fatty acid with polyglycerin is a non-ionic surfactant having an HLB of 5-15.

6. The oil-based liquid cleansing composition according to claim 3, wherein the ester of fatty acid with polyglycerin is contained by 5.0 to 25.0 percent by weight.

7. The oil-based liquid cleansing composition according to claim 3, wherein the ester of fatty acid with polyglycerin is selected from the group consisting of polyglycerin medium chain fatty acid esters produced by esterization of a medium chain fatty acid having a carbon number of 6 to 10 with a polyglycerin having an average degree of polymerization of 3 or above but less than 100.

8. The oil-based liquid cleansing composition according to claim 3, wherein the ester of fatty acid with polyglycerin is polyglycerin caprylate.

9. The oil-based liquid cleansing composition according to claim 3, which consists of oil-based components.

10. The oil-based liquid cleansing composition according to claim 1, wherein the monovalent fatty acid ester is octyl palmitate.

11. The oil-based liquid cleansing composition according to claim 3, wherein the monovalent fatty acid ester is octyl palmitate.

12. The oil-based liquid cleansing composition according to claim 3, which consists of the ester of fatty acid with polyglycerin, the glycerin ester of monocarboxylic acid with dicarboxylic acid, and the monovalent fatty acid ester.

* * * * *